United States Patent

Piriou et al.

[11] Patent Number: 5,914,595
[45] Date of Patent: Jun. 22, 1999

[54] EDDY CURRENT SENSOR AND TUBE TESTING TOOL HAVING AT LEAST ONE SUCH SENSOR

[75] Inventors: Marc Piriou, Vincennes; Jacky Slazak, Auneau, both of France

[73] Assignee: Intercontrole, Rungis Cedex, France

[21] Appl. No.: 08/913,894

[22] PCT Filed: Jan. 23, 1997

[86] PCT No.: PCT/FR97/00133

§ 371 Date: Sep. 17, 1997

§ 102(e) Date: Sep. 17, 1997

[87] PCT Pub. No.: WO97/27476

PCT Pub. Date: Jul. 31, 1997

[30] Foreign Application Priority Data

Jan. 24, 1996 [FR] France ................................ 96/00790

[51] Int. Cl.[6] ............................................. G01N 27/90
[52] U.S. Cl. ........................ 324/220; 324/232; 324/240
[58] Field of Search ................................... 324/219–221, 324/232, 239–243, 329

[56] References Cited

U.S. PATENT DOCUMENTS

| | | | |
|---|---|---|---|
| 2,124,579 | 7/1938 | Knerr et al. ...................... | 324/242 X |
| 2,807,777 | 9/1957 | Doll ................................... | 324/329 |
| 3,238,448 | 3/1966 | Wood et al. ...................... | 324/220 |
| 3,395,341 | 7/1968 | Malaquin ......................... | 324/239 X |
| 4,652,823 | 3/1987 | Sutton . | |
| 4,797,613 | 1/1989 | Wentzell .......................... | 324/220 |
| 5,119,023 | 6/1992 | Lloyd ............................... | 324/220 X |
| 5,134,367 | 7/1992 | Griffith et al. . | |

FOREIGN PATENT DOCUMENTS 370691   5/1990   European Pat. Off. .

*Primary Examiner*—Gerard Strecker
*Attorney, Agent, or Firm*—Pearne, Gordon, McCoy & Granger LLP

[57] ABSTRACT

For the nondestructive testing of an electrically conductive part (T), an eddy current sensor (22a) is proposed having two transmitter windings (26) and one receiver winding (28). These three windings are arranged symmetrically with respect to a reference plane (P1) oriented perpendicular to the surface of the part (T). The receiver winding (28) is placed between the active portions (26a) of the emitter windings (26) and perpendicular to the plane (P1), whereas the transmitter windings (26) are substantially parallel to said plane. The coils and connections of the transmitter windings are such that the receiver winding is not traversed by any current in the absence of a fault. A tool for testing a tube (T), such as a steam generator tube, has two sensors oriented at right angles to one another.

4 Claims, 2 Drawing Sheets

EDDY CURRENT SENSOR AND TUBE TESTING TOOL HAVING AT LEAST ONE SUCH SENSOR

DESCRIPTION

1. Technical Field

The invention relates to an eddy current sensor using separate receiver and transmitter windings for carrying out the nondestructive testing of electrically conductive parts.

The invention also relates to a tool for the nondestructive testing of tubes, said tool having at least one eddy current sensor.

The sensor according to the invention can be used for the nondestructive testing of a part having random shape and dimensions, provided that the nature of the material or materials constituting said part permit the induction therein of eddy currents. A preferred, but in no way limitative application, relates to the testing of steam generator tubes equipped nuclear power stations.

2. Prior Art

In view of their ease of implementation, eddy current sensors have been subject to numerous developments in the nondestructive testing field.

The principle of such sensors is based on creating a primary magnetic field in a winding supplied with alternating current. When the winding is placed in the vicinity of an electrically conductive material, said primary magnetic field induces eddy currents in the material. These eddy currents produce a secondary magnetic field opposing the primary magnetic field. The thus formed secondary magnetic field has the effect of modifying the impedance of the winding in proportions dependent on the value of the air gap between the winding and the part and the different factors linked with the shape and internal structure of the part. Nondestructive testing by means of eddy currents is essentially based on the fact that the presence of faults in the material modifies the impedance of the winding.

The simpler sensors have a single winding used both as the transmitter and as the receiver.

The most widely used sensors are employed in differential measurements. These sensors generally use two windings connected in series, both being used as transmitters and receivers. Due to the fact that the windings face two adjacent regions of the part, any impedance difference between the two windings reveals the presence of a fault in the material and also the extent thereof.

Eddy currents, whereof each winding acts both as a transmitter and a receiver, perform local measurements making it possible to establish the cartography of faults present within a part to be tested. However, such sensors only detect faults present over a limited depth from the surface of the part close to the measuring windings. Thus, in the case of the testing of tubes of steam generators, certain point sensors only detect faults on the outer wall when they have a depth exceeding 40% of the thickness of said wall.

EP-A-370 691 proposes testing a tube by means of an apparatus incorporating a single eddy current sensor fitted coaxially between two end parts. This sensor has two transmitter windings placed around a common axis to be located in accordance with the axis of the tube, as well as a plurality of receiver windings located in the annular gap separating the transmitter windings, so that their axes are oriented radially with respect to the axis of the transmitter windings. The latter are excited in opposition, so that the primary magnetic fields are summated in the gap containing the receiver windings. The detection cases place in turn on successive receiver windings, so as to perform a circumferential scan during the displacement of the apparatus in the tube.

Due to the fact that the primary magnetic fields are summated at the location of the receiver windings, the apparatus described in the aforementioned document requires an electronic compensation treatment in order to eliminate from the signals emitted by the receiver windings the fraction resulting from the summated primary magnetic fields.

The apparatus described in EP-A-370 691 is insensitive to cracks oriented in accordance with the circumference of the tube. Finally, this apparatus can only be used for the testing of a tube. It consequently does not permit the testing of parts having different shapes, such as plates.

DESCRIPTION OF THE INVENTION

The invention mainly relates to an originally designed eddy current sensor usable for the testing of parts having random shapes, in which the transmission and reception functions are ensured by separate windings, arranged in such a way that the fault detection performance characteristics are significantly increased compared with existing sensors (e.g. so as to detect faults on the outer wall having a depth limited to approximately 20% of the thickness of said wall, in the case of the testing of steam generator tubes) without it being necessary to have a subsequent compensation treatment.

According to the invention, this result is obtained by means of an eddy current sensor comprising two transmitter windings and at least one receiver winding arranged symmetrically relative to a reference plane oriented in a direction substantially perpendicular to a surface of a part to be tested, the transmitter windings being positioned on either side of the reference plane and each having a median plane substantially parallel to the reference plane and at least one active portion having a shape substantially complimentary of that of the surface, the receiver winding being oriented perpendicular to the reference plane between the active portions of the transmitter windings and having a median plane forming with the reference plane an angle of approximately 90°, characterized in that the transmitter windings are connected and wound in such a way that they induce opposing magnetic fields in a spatial zone containing the receiver winding, so that no current flows through the latter when the region of the part to be tested facing the sensor is free from any fault.

In the sensor according to the invention, the performance of the transmission and reception functions by separate windings and the special arrangement of these windings permits a significant increase in the resolution or detection depth of the sensor, whilst retaining performance characteristics comparable to those of existing, local detection sensors.

Moreover, due to the fact that the direction of the transmitter windings and the electrical connection thereof are such that said windings induce opposing primary magnetic fields at the location of the receiver winding, the signal supplied by the latter is directly representative of the presence of a possible fault, without it being necessary to carry out a subsequent compensation treatment.

Preferably, each transmitter winding has a single active portion corresponding to a circumferential fraction of said winding, the sensor having a single receiver winding positioned between said active portions. This feature makes it possible to test parts having random shapes, i.e. both tubes and plates.

The invention also relates to a tool for the nondestructive testing of a tube and which can be displaced within the latter. This tool has a central rotary body with a longitudinal axis and two centering rings supporting the body in the tube, so that the axis of the body substantially coincides with that of the tube. The central rotary body then supports at least one eddy current sensor, as defined hereinbefore.

In a preferred embodiment making it possible to detect any type of fault in the tube over a significant depth, the central rotary body supports a first sensor, whose reference plane is perpendicular to the longitudinal axis of the body and a second sensor, whose reference plane contains the longitudinal axis of the body.

Advantageously, the first and second sensors are then fitted on the central rotary body at diametrically opposite locations with respect to the longitudinal axis of the body.

BRIEF DESCRIPTION OF THE DRAWINGS

The invention is described in greater detail hereinafter relative to non-limitative embodiments and with reference to the attached drawings, wherein show.

DETAILED DESCRIPTION OF PREFERRED EMBODIMENTS

Figure 1:
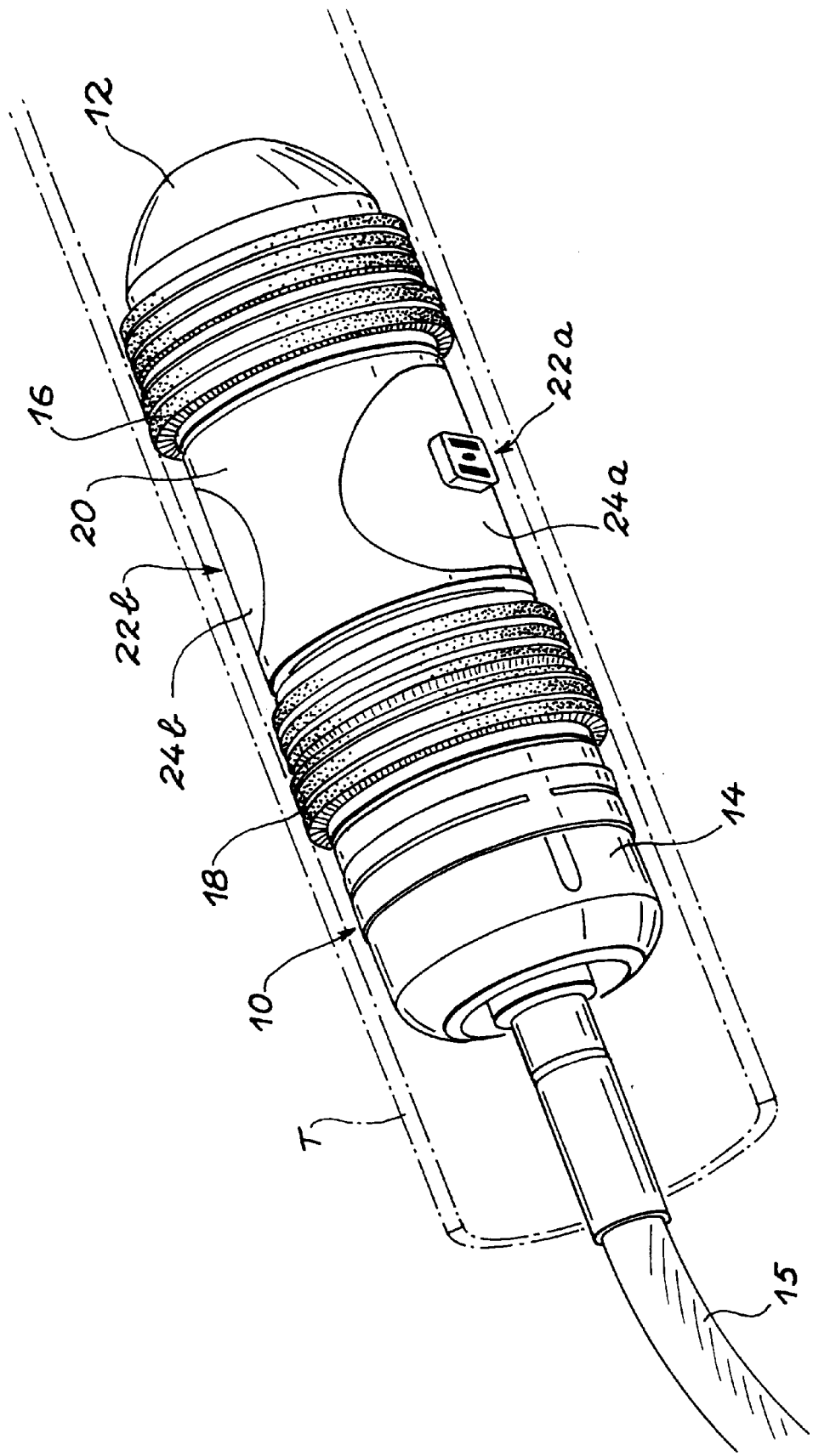
FIG. 1 A perspective view diagrammatically showing a tool equipped with two eddy current sensors according to the invention and which can be introduced into a steam generator tube in order to non-destructively test the same.

FIG. 1 shows a tube section T (shown in phantom lines), which is to undergo nondestructive testing. This tube section can in particular form part of a steam generator equipping a nuclear power station. Thus, the corrosive environment in which steam generator tubes are located requires regular testing for detecting any deterioration requiring sealing or repair of the tubes in question. As steam generator tubes are only accessible from the interior, their nondestructive testing conventionally takes place by the displacement within each of the tubes of an appropriate testing tool, so that there is an effective scan of the tube wall.

FIG. 1 shows as a non-limitative embodiment, a tool 10 for the nondestructive testing of the tube T using two eddy current sensors according to the invention. However, it is pointed out that the eddy current sensors according to the invention can be used for any nondestructive testing type. Thus, these sensors can be used both for the testing of a tubular part from the interior thereof and for the testing of parts having random other shapes such as flat parts or random profiles from faces of said parts.

The nondestructive testing tool 10 illustrated in FIG. 1 has a known overall configuration not forming part of the invention. To facilitate understanding, merely the general features thereof will be described.

The nondestructive testing tool 10 is substantially shaped like a cylinder, whose longitudinal axis is intended to substantially coincide with that of the tube T. It has a nose cone-shaped front body 12 facilitating its penetration into the tube T, as well as a rear body 14 by which the tool is connected to a not shown, external installation across a flexible cable 15. This flexible cable 15 makes it possible to control the displacements of the tool 10 in the tube T and transmit between said tool and the external installation the electrical signals necessary for testing purposes.

The front body 12 and rear body 14 are non-rotary elements both supporting a flexible centering ring 16, 18 by means of which the tool 10 is centered in the tube T.

In its intermediate portion located between the centering rings 16 and 18, the nondestructive testing tool 10 has a central rotary body 20 centered on the longitudinal axis of the tool and which can be rotated at a constant speed about said axis during the displacement of the latter within the tube T. The rotation of the central body 20 is controlled by a not shown motor located in the rear body 14.

In the embodiment shown in exemplified manner in FIG. 1, the central rotary body 20 of the nondestructive testing tool 10 carries two eddy current sensors 22a, 22b. These two sensors 22a, 22b are located on the central body 20 at diametrically opposite locations with respect to the longitudinal axis of the tool. Therefore the sensor 22b is not visible in FIG. 1.

The combined translatory and rotary movements of the central portion 20 the tool 10 have the effect of displacing the sensors 22a and 22b in a helical movement within the tube T. Thus a scan of its wall is ensured.

To ensure the electrical insulation of each of the sensors, the portions 24a and 24b of the central body 20 surrounding the sensors 22a and 22b are made from an electrically insulating material.

A description will now be given with reference to FIGS. 2 and 3 of the eddy current sensor 22a equipping the tool 10 of FIG. 1.

Figure 2:
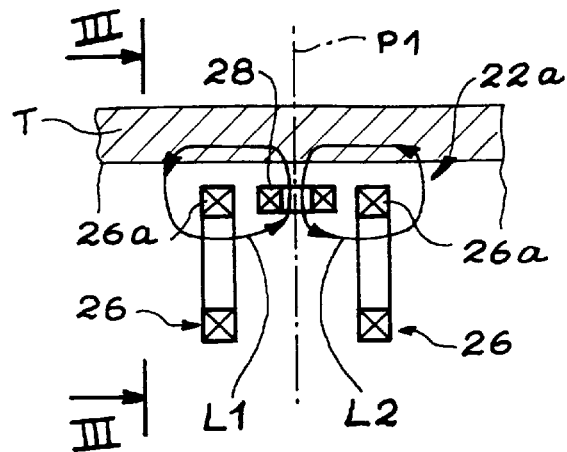
FIG. 2 A sectional view diagrammatically illustrating one of the sensors mounted on the tool of FIG. 1, as well as the facing tube portion.
Figure 3:
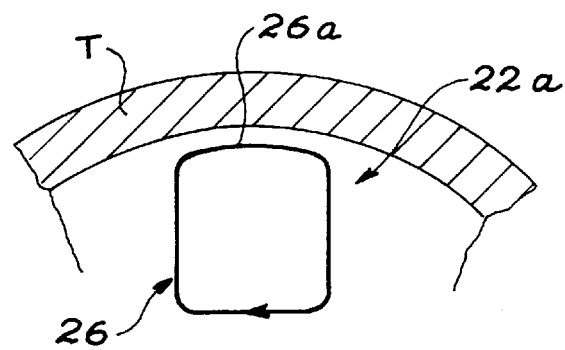
FIG. 3 A sectional view along line III—III of FIG. 2.

As is diagrammatically illustrated in FIGS. 2 and 3, said sensor 22a has two transmitter windings 26 and one receiver winding 28. The transmitter windings 26 are positioned symmetrically on either side of a reference plane P1 oriented perpendicular to the inner surface of the tube T, i.e. in the case of the sensor 22a perpendicular to the axis of the tube T. In the same way, the reference plane P1 constitutes a plane of symmetry for the receiver winding 28.

More specifically, by using the term "median plane" of each of the windings 26, 28 for designating the plane containing the central wire of said winding, the median planes of the transmitter windings 26 are arranged substantially parallel to the reference plane P1 on either side of the latter. Moreover, the median plane of the receiver winding 28 is oriented perpendicular to the reference plane P1. Moreover, the dimensions of the receiver winding 28 are substantially smaller than those of the transmitter windings 26.

As is more particularly illustrated in FIG. 3, each of the transmitter windings 26 has an active portion 26a corresponding to a circumferential fraction of said winding and having a shape complementary of that of the inner surface of the tube T. Due to the fact that the median planes of the transmitter windings 26 are parallel to the reference plane P1 oriented perpendicular to the axis of the tube T, said active portions 26a of the transmitter windings 26 have in this case a circular arc shape. Over the remainder of the circumference of the transmitter windings, they can assume random shapes.

According to another aspect of the invention, the receiver winding 28 is placed between the active portions 26a of the transmitter windings 26.

The transmitter windings 26 are electrically connected in series so as to be simultaneously supplied by the same alternating current having a random shape (sinusoidal, pulsed, etc.). The primary magnetic fields produced in this way by the two transmitter windings 26 create field lanes L1, L2, whereof one portion passes into the wall of the tube T facing the active portions 26a of the transmitter windings 26. The geometrical configuration of the eddy current sensor 22a according to the invention described hereinbefore is such that the receiver winding 28 is located in the center of said field lines L1, L2.

Moreover, the electrical connection of the transmitter windings 26 and the direction of their coils are such that the primary magnetic fields which they produce are oriented in opposite directions in the spatial zone in which the receiver winding 28 is located. Due to the perfect symmetry of the sensor and the above-described arrangement, no current flows through the receiver winding 28 for as long as the region of the tube T facing said sensor is fault-free. The current flowing in the receiver winding 28 consequently directly represents a fault present in the region of the tube facing the sensor, without it being necessary to carry out any subsequent electrical treatment.

It should be noted that this result can be obtained either by winding the two transmitter windings 26 in the same direction and directly connecting them in series, or by winding them in the opposite direction and connecting them in opposition, so that they are always excited in opposite directions.

Due to this arrangement, the receiving winding 28 is insensitive to the permanent state of the secondary magnetic field created by the eddy currents induced in the primary tube T. Thus, the receiver winding 28 only detects variations of the secondary magnetic field due to the presence of faults in the thickness of the wall of the tube T. More specifically, the orientation of the eddy current sensor 22a illustrated in FIGS. 2 and 3 makes it possible to detect cracks, which mainly extend in accordance with the longitudinal axis of the tube T.

The particular characteristics of the eddy current sensor according to the invention and in particular its insensitivity to the permanent secondary magnetic field enable it to detect faults over a significantly greater depth than existing eddy current sensors. Thus, the sensor according to the invention detects faults to approximately 80% of the depth of the wall of the tube T, whereas existing sensors only detect such faults over a depth less than 60% of said thickness.

Due to the fact that the eddy current sensor 22a is insensitive to cracks oriented in accordance with the circumference of the tube T, the tool 10 illustrated in FIG. 1 advantageously has a second eddy current sensor 22b constructed according to the same principle as the sensor 22a, but whose orientation is displaced by 90° relative to the latter.

Figure 4:
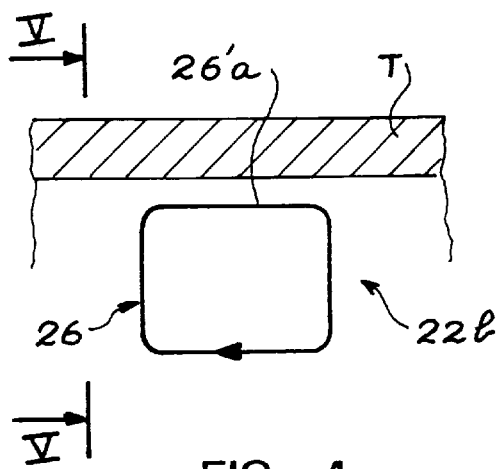
FIG. 4 A diagrammatic sectional view comparable to FIG. 2 illustrating the second sensor of the tool of FIG. 1.
Figure 5:
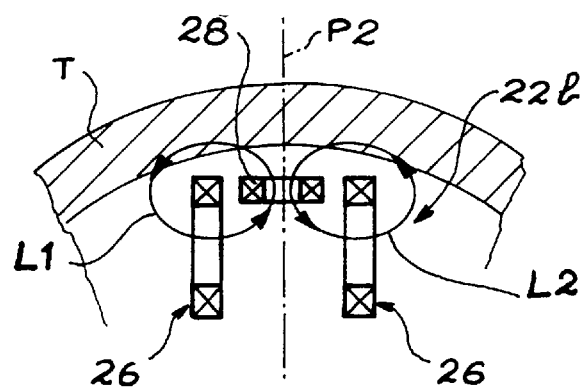
FIG. 5 A sectional view along line V—V of FIG 4.

Thus, as illustrated in FIGS. 4 and 5, the sensor 22b also has two transmitter windings 26 and a receiver winding 28, whose relative arrangement is the same as that of the comparable windings of the sensor 22a. More specifically, the said three windings 26 and 28 are also arranged symmetrically with respect to a reference plane P2. However, said reference plane P2 is perpendicular to the reference plane P1 of the sensor 22a. More specifically, this reference plane P2 in this case contains the longitudinal axis of the tool.

Due to the fact that the median planes of the transmitter windings 26 are parallel to the reference plane P2, the active portions 26'a of said transmitter windings are in this case oriented parallel to generatrixes of the tube T. Thus, said active portions are rectilinear, as illustrated in FIG 4.

As in the case of the sensor 22a, the transmitter windings 26 of the sensor 22b are electrically connected and wound in a direction such that the primary magnetic fields which they produce when excited are oriented in opposite directions in the region of the receiver winding 28. This feature, illustrated by the field lines L1 and L2 in FIG. 5, makes it possible to obtain an output signal of the receiver winding 28 directly representative of the presence of a fault, without requiring any subsequent treatment.

Due to its orientation, the sensor 22b is sensitive to faults oriented circumferentially in the tube T. Thus, the assembly formed by the sensors 22a and 22b makes it possible to detect any fault type in the tube T over a significantly greater depth than existing sensors and without requiring any treatment for eliminating a d.c. component of signals supplied by the sensors, because said component does not exist.

We claim:

1. Tool for the nondestructive testing of a tube and which can be displaced within the latter, comprising a central rotary body having a longitudinal axis and two centering rings supporting the body in the tube in such a way that the body axis substantially coincides with the tube axis, wherein the central rotary body supports at least one eddy current sensor comprising two transmitter windings and at least one receiver winding arranged symmetrically with respect to a reference plane to be oriented in accordance with a direction substantially perpendicular to a surface to be tested, the transmitter windings being positioned on either side the reference plane and each having a median plane substantially parallel to the reference plane and at least one active portion having a shape substantially complementary to that of the surface, and the receiver winding is oriented perpendicular to the reference plane and placed between the active portions of the transmitter windings and having a median plane forming with the reference plane an angle of approximately 90°, wherein the two transmitter windings are connected and wound in such a way that they induce opposing magnetic fields in a spatial zone containing the receiver winding, so that no current flows through the latter when the region of the surface to be tested facing the sensor is fault-free.

2. Tool according to claim 1, wherein each transmitter winding has a single active portion corresponding to a circumferential fraction of said winding, the sensor having a single receiver winding located between these active portions.

3. Tool according to claim 1, wherein the central rotary body supports a first sensor, whose reference plane is perpendicular to the longitudinal axis of the body and a second sensor, whose reference plane contains the longitudinal axis of the body.

4. Tool according to claim 3, wherein the first and second sensors are mounted on the central rotary body at diametrically opposite locations with respect to the longitudinal axis of the body.

* * * * *

UNITED STATES PATENT AND TRADEMARK OFFICE
CERTIFICATE OF CORRECTION

PATENT NO.   : 5,914,595
DATED        : June 22, 1999
INVENTOR(S)  : Piriou et al.

It is certified that error appears in the above-identified patent and that said Letters Patent is hereby corrected as shown below:

Column 2, Line 37, delete "complimentary" and insert --complementary--.

Column 4, Line 25, after "20", insert --of--.

Column 4, Line 27, after "Thus", insert --,-- (comma).

Signed and Sealed this

Ninth Day of November, 1999

Attest:

Attesting Officer

Q. TODD DICKINSON

Acting Commissioner of Patents and Trademarks